United States Patent
Brandstaetter et al.

(10) Patent No.: US 8,809,510 B2
(45) Date of Patent: Aug. 19, 2014

(54) METHOD FOR PURIFICATION OF COMPLEMENT FACTOR H

(75) Inventors: Hubert Brandstaetter, Vienna (AT); Petra Schulz, Eichgraben (AT); Juergen Roemisch, Gramatneusiedl (AT)

(73) Assignee: Octapharma AG, Lachen (CH)

( * ) Notice: Subject to any disclaimer, the term of this patent is extended or adjusted under 35 U.S.C. 154(b) by 0 days.

(21) Appl. No.: 13/879,283

(22) PCT Filed: Oct. 13, 2011

(86) PCT No.: PCT/EP2011/067883
§ 371 (c)(1),
(2), (4) Date: Apr. 12, 2013

(87) PCT Pub. No.: WO2012/049245
PCT Pub. Date: Apr. 19, 2012

(65) Prior Publication Data
US 2013/0203971 A1 Aug. 8, 2013

Related U.S. Application Data

(60) Provisional application No. 61/344,805, filed on Oct. 13, 2010.

(30) Foreign Application Priority Data

Oct. 13, 2010 (EP) .................................. 10187410

(51) Int. Cl.
| | |
|---|---|
| C07K 1/18 | (2006.01) |
| A61K 38/00 | (2006.01) |
| G01N 30/02 | (2006.01) |
| C07K 1/22 | (2006.01) |
| C07K 1/36 | (2006.01) |
| A61K 39/00 | (2006.01) |
| C07K 14/705 | (2006.01) |
| A61K 35/16 | (2006.01) |
| C07K 14/47 | (2006.01) |

(52) U.S. Cl.
USPC ............ 530/416; 530/380; 530/395; 530/412

(58) Field of Classification Search
None
See application file for complete search history.

(56) References Cited

U.S. PATENT DOCUMENTS

2008/0318841 A1  12/2008  Chtourou et al.
2009/0118163 A1*  5/2009  Gronski et al. ................... 514/8

FOREIGN PATENT DOCUMENTS

| DE | WO2008113589 | * | 9/2008 | ............. C07K 14/47 |
| EP | 0893450 A1 | | 1/1999 | |
| WO | WO-2005/082937 A2 | | 9/2005 | |
| WO | WO-2008/113589 A1 | | 9/2008 | |

OTHER PUBLICATIONS

Warwicker et al. "Familial relapsing haemolytic uraemic syndrome and complement factor H deficiency" 1999 Nephrol Dial Transplant 14 1229-1233.*
Lundwall et al., "Isolation of Human Complement Factors C3, C5 and H", Journal of Immunological Methods, 81 (1985) 147-160.
Nagasawa et al., Cleavage of C4b by C3b Inactivator: Production of a Nicked Form of C4b, C4b', as an Intermediate Cleavage Product og C4b by C3b Inactivator, Journal of Immunology, vol. 125, No. 2, Aug. 1980, p. 578-582.
Crossley et al., "Purification of the Human complement control protrin C3b inactivator", Biochem. J. (1980) 191, 173-182.
Weiler et al., "Control of the amplification convertase of complement by the plasma protein β1H", Proc. Natl. Acad. Sci. USA, vol. 73, No. 9, pp. 3268-3272, Sep. 1976.
Mhatre et al., "Isolation of bovine complement factor H.", Vet. Immunol. Imminopathol., 14: 357-375, 1987.
International Search Report and Written Opinion in Application No. PCT/EP2011/067883, mailed Dec. 22, 2011.

* cited by examiner

*Primary Examiner* — Suzanne M Noakes
*Assistant Examiner* — Gerard Lacouriere
(74) *Attorney, Agent, or Firm* — Venable LLP; Nancy J. Axelrod; Michael A. Gollin

(57) ABSTRACT

A method for purification of complement Factor H from a complement Factor H containing source such as blood or blood plasma, in particular a caprylate precipitate of a Factor H containing source, which is e.g. obtained by addition of caprylate ions to fractions of blood or plasma, comprising the steps of:
a) providing a Factor H containing source, in particular reconstitution of caprylate precipitate to provide a complement Factor H containing solution;
b) performing a cation exchange chromatography in particular as first chromatographic step;
c) performing an anion exchange chromatography;
d) performing a hydroxyl apatite chromatography;
e) followed by ultra/diafiltration to obtain a complement Factor H concentrate.

5 Claims, 2 Drawing Sheets

METHOD FOR PURIFICATION OF COMPLEMENT FACTOR H

CROSS-REFERENCE TO RELATED APPLICATIONS

Figure 1:
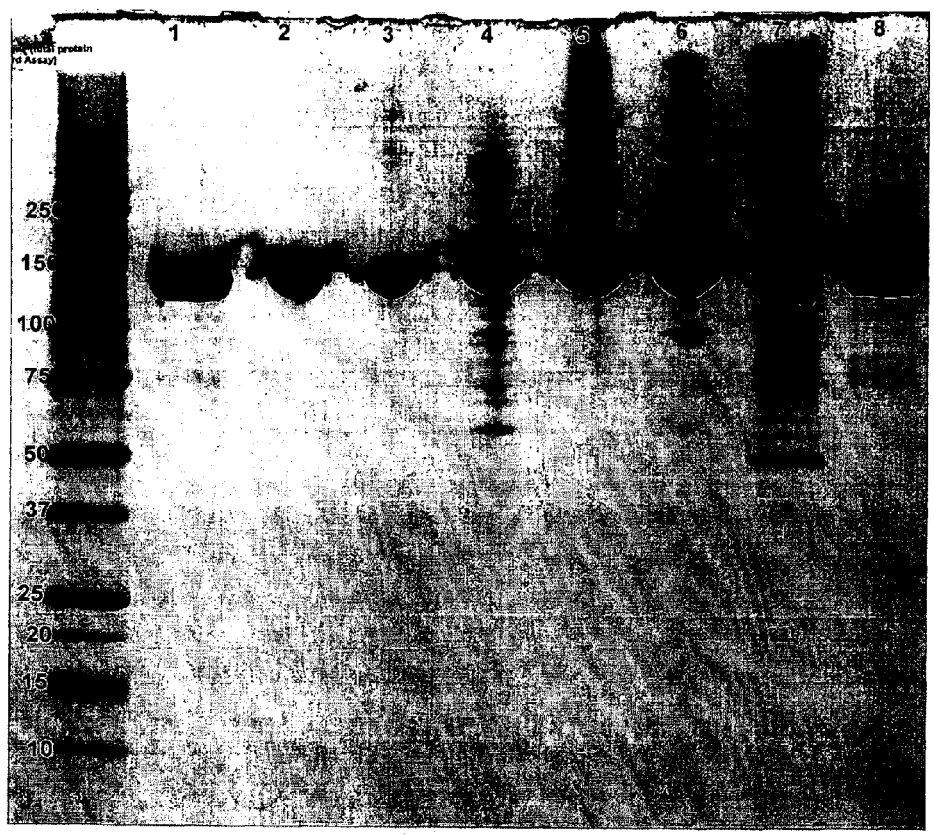

This application is a U.S. National Stage of Application No. PCT/EP2011/067883, filed Oct. 13, 2011, which claims priority to U.S. Provisional Application No. 61/344,805, filed Oct. 13, 2010, and European Application No. 10187410.5 filed Oct. 13, 2010, the entire contents of which are hereby incorporated by reference.

This invention provides a method for purification of complement Factor H of high purity and biological activity from a Factor H containing material. The resulting plasmatic complement Factor H concentrate can be utilized as therapeutic complement inhibitor in pathologic conditions, in particular those involving abnormal activation of the alternative complement system.

INTRODUCTION

The complement Factor H is a plasmatic glycoprotein of mainly hepatic source that was first discovered by Nilsson and Mueller-Eberhard (1965), J Exp Med, 122, 277-298). It consists of a repeated sequence of 20 short consensus repeats (SRC) or complement control proteins (CCP) of 60 amino acids each. Proteins consisting of SCR modules are discussed to be structurally stable molecules. Exposure of complement Factor H to different harsh chemical and physical conditions did not abrogate its activity (Kask et al. (2004) Protein Sci. 13, 1356-1364).

It is an essential regulator of the alternative pathway of complement by means of several molecular mechanisms. First, complement Factor H acts as an essential co-factor for Factor I-mediated cleavage of activated complement component 3b (C3b). Second, it competes with Factor B fragment Bb for binding to C3b thereby inhibiting the formation of C3 convertase comprising a complex of C3b and Bb and thus the initiation of complement amplification.

Third, the molecular architecture of complement Factor H bearing several different binding domains for ligands on different short consensus repeats (SCR) enables the discrimination between host and non-host by differential binding avidity. In other words, by provision of sufficient binding avidity towards surfaces carrying sufficient ligands, complement Factor H is able to discriminate at which surface to prevent complement activation (host) and at which not (e.g. pathogen) (Meri and Pangburn (1990) PNAS 87, 3982-3986).

Complement Factor H has been evidenced to be involved in several pathophysiological conditions with abnormal activation of the alternative pathway of complement, namely Membranoproliferative Glomerulonephritis type II (also termed Dense Deposit Disease; reviewed in Pickering and Cook, Clin Exp Immunol (2008), 151, 210-230), Atypical Hemolytic Uremic Syndrome (reviewed in Noris and Remuzzi, Clin Exp Immunol (2008), 151, 199-209) and importantly, Age-Related Macular Degeneration (Hageman et al. (2005) PNAS 102, 7227-7232).

Evidence was provided that a tyrosine-to-histidine amino acid exchange at position 402 of complement Factor H (Y402H), with a prominent heterozygous prevalence of 30% in healthy western populations, predisposes individuals to Age-related Macular Degeneration (AMD) (Hageman, G. S. et al., Proc Natl Acad Sci USA 102, 7227-7232, (2005); Edwards, A. O. et al., Science 308, 421-424, (2005); Klein, R. J. et al., Science 308, 385-389, (2005); Haines, J. L. et al., Science 308, 419-421, (2005)). The complement Factor H 402H risk variant augments the risk of developing AMD 2-4 fold for heterozygote and 5-7 fold for homozygote individuals. The Y402H polymorphism was found to render complement Factor H dysfunctional in terms of reduced binding (Clark, S. J. et al., Biochem Soc Trans., 2010, 38, 1342-8; Kelly, U. et al., J Immunol., 2010, 185, 5486-94) and complement regulation at sites of injury (Lauer, N. et al., J Immunol., 2011). Given the major impact of complement in AMD pathoetiology (Anderson, D. H. et al., Prog Retin Eye Res., 2010, 29, 95-112), it is highly tempting to investigate the value of purified CFH as therapeutic complement inhibitor in the treatment of AMD patients, especially those individuals expressing the CFH risk variants.

Furthermore, manifold experimental data provide evidence for an involvement of the alternative complement pathway in certain pathologies that strongly suggests the usage of complement inhibitors to efficiently regulate the underlying abrogated complement activation. Pathologies discussed to be treated by complement inhibitors comprise Ischemia Reperfusion Injury (Huang et al. (2008) J Immunol 181, 8068-8076; Stahl et al. (2003) J Pathol 162, 449-455), Chronic Nephropathies due to proteinuria with abnormal complement activation in the proximal tubules (He et al. (2005) J Immunol 174, 5750-5757; Abbate et al. (2008) J Am Soc Nephrol 19, 1158-1167 or autoimmune encephalomyelitis (Griffiths et al. (2009) J Immunol 182, 4368-4377).

Empirically, therapy for patients suffering from Atypical Hemolytic Uremic Syndrome consists of plasma manipulation (plasma infusion or plasmapheresis) with the rationale to correct the patient's deficiency of functional complement Factor H molecules (Noris and Remuzzi, Clin Exp Immunol (2008), 151, 210-230). However, this type of treatment is accompanied by certain disadvantages the large plasma volumes needed to administer an appropriate amount of functional Factor H.

There are very few reports about therapy for human Dense Deposit Disease (Licht C et al. (2006) Kidney Int., 70, 42-50). Recently, the first in vivo evidence for complement Factor H to serve as therapeutic means in a mouse model of Dense Deposit Disease was provided (Fakhouri et al. (2010) Kidney Int., 1-8). Therein, a plasmatic complement Factor H concentrate, elaborated by multi-step chromatography, completely ameliorated the renal lesions induced by the complete absence of complement Factor H and was finally discussed by these authors to be an effective alternative treatment to plasma therapy in patients of Dense Deposit Disease.

To date, no treatment for dry form of age-related macular degeneration, the world's leading cause of legal blindness of the elderly population, exists. Approximately 90% of individuals developing early-onset macular degeneration clinically demonstrate the non-neovascular dry form characterized by atrophy of the Retinal Pigmented Epithelium and loss of macular photoreceptors (Klein et al. (2004) Am J Ophthalmol. 137, 486-495). One certain haplotype of complement Factor H gene can be found heterozygously in approximately 30% of the population and is present in more than 50% of patients with dry form age-related macular degeneration (Hageman et al. (2005) PNAS 102, 7227-7232). This single nucleotide polymorphism in complement Factor H gene exchanges a tyrosine towards histidine at position 402 (Y402H) of the protein and leads to a reduced binding capacity of complement Factor H for polyanions and other natural ligands (Laine et al. (2007) J Immunol 178, 3831-3836). Thus, every third person of the normal population is carrier of a 3-fold increased risk of developing age-related macular degeneration while every tenth person carries an eighth-fold increased risk reflected by a prevalence of homozygous carriers of Y402H of 10%. Additionally, recent data demonstrate various complement components and inhibitors to form integral part of the hallmark extracellular retinal deposits, termed drusen, playing a pivotal role in drusen formation (Anderson et al. (2010) Prog Ret Eye Res 29, 95-112). The important role of complement in age-related macular degeneration (AMD) pathogenesis therefore strongly suggests the therapeutic utilization of complement-modulating agents. Especially, the lack of natural endogenous complement regulators in affected retinal tissues (RPE and Bruch's membrane) and the established role of the local retinal complement system in AMD pathogenesis shed light on potential usage of complement Factor H as therapeutic means for dry-form AMD. Application of complement Factor H for that purpose can thus be suggested to be achieved preferably by intraocular injection or intravenously on a regular basis.

The impact of this single nucleotide polymorphism on the function of Factor H is under investigation, but it is very likely to affect its regulatory function in several disease states. Therefore, the application of functional Factor H to such patients, but not limited to, is probable to support healing.

Currently, any pharmaceutical composition of complement Factor H is commercially available to be administered to patients suffering from diseases related to complement Factor H deficiency, examples of such diseases are discussed above. It is therefore an objective of this invention to provide a Factor H concentrate and a corresponding manufacturing process from a suitable Factor H source, which is selected from blood or blood plasma and their derived fractions, recombinantly produced Factor H, preferably by a human cell-line like Human Embryonic Kidney cells (HEK), or transgenically expressed protein.

A possible source for the purification of a complement Factor H concentrate is human blood plasma which abundantly contains complement Factor H in a concentration of about 500 µg/ml.

Carron et al., Biochimica et Biophysica Acta, General Subjects (1996), 1289(3), 305-11 discloses Factor H purification by activating human platelets with thrombin and subjecting the supernatant to a gelatin purification, for removal of fibronectin, and heparin sepharose. Elution of Factor H was accomplished by a 0.3M NaCl buffer and further purified by DEAE-chromatography. A second pathway is described starting from plasma successively followed by chromatographies on L-lysin-Sepharose, DEAE-Sephagel and a selective Factor H-antibody affinity chromatography.

Lundwall et al., Journal of Immunological Methods (1985), 81(1), 147-60 describes the isolation of Factor H by suspending QAE-Sephadex twice in plasma, overlaying the once suspended QAE-Sephadex on already packed QAE-Sepadex columns and elution of the Factor H containing fraction. This fraction is afterwards loaded on a SP-Sephadex column before a final chromatography on DEAE-Sephacel is performed to obtain complement Factor H. Plasmin and/or plasminogen were assumed as possible impurities.

US 2008/318841 A1 discloses the purification of Factor H from the supernatant of plasma cryoprecipitate. Submission of the supernatant to anion exchange chromatography is followed by application of the non-retained fraction to a first heparin affinity chromatography. Non-bound Factor H is applied to a second heparin-affinity chromatography under binding conditions and after elution subjected to a first anion exchange chromatography. After elution of Factor H a second anion exchange chromatography is performed before concentrating Factor H.

WO 2008/113589 A1 refers to the purification of Factor H by various methods comprising one or more chromatographic steps selected from heparin affinity chromatography, hydrophobic interaction chromatography (HIC), anion exchange chromatography (AEC), cation exchange chromatography, hydroxyapatite chromatography (HAC) or immunoaffinity chromatography.

Nagasawa S. et al. report about cleavage of complement C4b by complement C3b inactivator production of a nicked form of complement C4b, complement C4b as an intermediate cleavage product of complement C4b by complement C3b in activator in Journal of Immunology, Vol. 125, No. 2, 1980, pages 578-582. A disclosed purification of complement C3b inactivator, i.e. human complement factor I, from plasma comprises cation exchange chromatography, anion exchange chromatography followed by heparin chromatography.

Mhatre A. et al. discloses the isolation of bovine complement factor H in Veterinary Immunology and Immunopathology, Vol. 14, No. 4, pages 357-375. The isolation of bovine complement factor H from serum is reported. The isolation method comprises a PEG precipitation, followed by anion exchange chromatography, cation exchange chromatography and concentration by ultracentrifugation.

SUMMARY OF THE INVENTION

An object of the present invention is to provide a method for purification of Factor H from Factor H containing sources. Another object is to provide a concentrate of Factor H in particular for pharmaceutical purposes.

The present invention discloses a method for purification of complement Factor H from a complement Factor H containing source such as blood or blood plasma, in particular a caprylate precipitate of a Factor H containing source, which is e.g. obtained by addition of caprylate ions to fractions of blood or plasma, comprising the steps of:

a) Providing a Factor H containing source, in particular reconstitution of a caprylate precipitate to provide a complement Factor H containing solution;

b) performing a cation exchange chromatography in particular as first chromatographic step;

c) performing an anion exchange chromatography;

d) performing chromatography over hydroxyl-apatite;

e) followed by ultra/diafiltration to obtain a complement Factor H concentrate.

According to one embodiment of the invention a heparin affinity chromatography is performed in addition.

In a further embodiment the process of the invention comprises at least one of the following methods for pathogen removal and/or inactivation:

a) solvent/detergent treatment;

b) pasteurization, c) vapor heat treatment;

d) dry heat treatment;

e) nanofiltration.

In still another embodiment the method of the invention the complement Factor H concentrate is lyophilized, optionally together with pharmaceutically acceptable substances for formulation.

In still another embodiment the invention pertains to a complement Factor H obtainable by a method according to the invention. Such Factor H is characterized by its high purity and activity.

In particular, the complement Factor H of the invention is obtainable by a method comprising
a) reconstitution of caprylate precipitate to provide a complement Factor H containing solution;
b) performing virus inactivation by solvent/detergent treatment (S/D treatment).
c) performing a cation exchange chromatography chromatographic step under the following conditions:
binding of complement Factor H to a strong cation exchange resin of the sulphopropyl type, washing with a buffer comprising of 20 mM tri-sodium citrate adjusted to pH 6.0 and elution of complement Factor H with an elution buffer comprising of 20 mM tri-sodium citrate and 0.2 M NaCl adjusted to pH 6.0;
d) performing an anion exchange chromatography step under the following conditions:
applying of the complement Factor H containing solution (conductivity 0.1-0.5 mS/cm) to a strong anion exchange resin of the quaternary ammonium type, washing with a buffer comprising of 20 mM Tris adjusted to pH 8.6 and elution of complement Factor H with an elution buffer comprising of 20 mM Tris and 0.2M NaCl adjusted to pH 8.6;
e) performing a ceramic hydroxyl apatite chromatography by loading the fraction of step d) on the ceramic hydroxyl apatite, optionally after an exchange of the buffer of step d) has been performed, and elution with a linear gradient of sodium chloride up to 1 M NaCl and collecting fractions eluting at a conductivity of the buffer in the range of 70-100 mS/cm;
f) optionally performing a heparin affinity chromatography step under the following conditions: applying of the complement Factor H containing solution to a resin with heparin immobilized on the surface, washing with a buffer comprising 20 mM tri-sodium citrate adjusted to pH 6.0 and elution of complement Factor H with an elution buffer comprising of 20 mM tri-sodium citrate and 0.2M NaCl adjusted to pH 6.0;
g) followed by ultra/diafiltration to obtain a complement Factor H concentrate, optionally a step of nanofiltration can be provided and may serve as virus removal step.

The complement Factor H of the invention is further characterized by being a liquid or lyophilized preparation.

In yet another embodiment of the invention the complement Factor H of the invention can be used for treating of a disease related to complement Factor H deficiency or abnormal activity. In particular, the disease is selected from the group consisting of Membranoproliferative Glomerulonephritis, Dense Deposit Disease, Hemolytic Uremic Syndrom, Atypical Hemolytic Uremic Syndrom or Age-related Macular Degeneration. Additionally the complement Factor H according to the invention can be used for the manufacture of a medicament to treat Ischemia Reperfusion Injury, Chronic Nephropathy or Autoimmune Encephalomyelitis.

FIG. 1 depicts a 4-20% TRIS-glycine gradient SDS-Page with 5 μg of various proteins applied per each lane and with silver staining.

FIGS. 2A-2D depict densitometric measurements of lanes 1 to 3 and the marker lane of FIG. 1. By nature of the silver stained SDS-Page it is possible to visualize trace amounts of proteins but a densitometric quantification of peaks is not possible. The densitometric measurement was undertaken to improve visualization of impurities for purely qualitative reasons as reprinting of FIG. 1 might lead to loss of information.

It is clarified that the wording "comprising" used in the present application is to be understood as also including the meaning of "consisting".

DETAILED DESCRIPTION OF THE INVENTION

The present invention provides a purification method for complement Factor H from any Factor H source, preferably from fractions of plasma fractionation. Examples for such fractions are reconstituted fraction I+II+III precipitate and fraction I+III precipitate, which is obtained from reconstituted fraction I+II+III precipitate, and refer to fractions obtained from cold ethanol fractionation processes. These processes, such as Cohn, Kistler-Nitschmann and their modifications are known to the skilled person.

Surprisingly it was found that a precipitate obtained by caprylate precipitation, for example performed as described in WO 2005/082937, i.e. dissolution of Cohn fraction I+II+III or fraction II+III in water, adjustment of pH to about 4.9 with acetic acid and precipitation by addition of caprylate while the pH is kept constant, contains functional Factor H and that an active concentrate of high purity Factor H can be obtained from this intermediate. It is understood to a skilled person that equivalent intermediates such as those obtainable from the Kistler-Nitschmann or Hink fractionation procedure or modifications thereof are also suitable. The purification process of this invention is supplemented with at least one effective and dedicated pathogen removal, reduction or inactivation method such as pasteurization, vapor heat treatment, solvent-detergent treatment, in particular Triton/TnBP, or nanofiltration, in particular through filters <35 nm pore size, most preferably ≤20 nm. The term 'pathogen' as used herein refers to, but is not limited to, viruses, e.g. HIV, Parvo or various forms of Hepatitis, fungi, bacteria and/or prions, e.g. $PrP^{Sc}$. In addition, final container dry-heating of a freeze-dried Factor H concentrate can be performed and described steps for inactivation and/or removal can be combined.

Starting material for the method of purification of Factor H are fractions from a plasma fractionation process. One possible Factor H-rich plasma protein fraction is reconstituted Fraction I+II+III precipitate from a Cohn fractionation procedure. Fraction I+II+III precipitate is obtained by subjecting a conventional cryoprecipitate supernatant from fresh frozen plasma to cold ethanol precipitation. In addition to immunoglobulins, Fraction I+II+III of the Cohn process contains several lipoproteins, fibrinogen and several proteins involved in fibrinolytic systems and various minor components. A paste prepared from fraction I+II+III or fraction II+III by caprylate precipitation, as described in WO 2005/082937 A1 (shortly described above) or EP 0 893 450 A1, reconstitution of fraction I+II+III or fraction II+III at pH 3.8-4.5 is followed by addition of caprylate and/or caprylic acid thus causing a pH shift to 5.0-5.2 and precipitation of proteins. Precipitates prepared according to WO 2005/082937A1 or EP 0893 450 A1 are examples of caprylate precipitates that can advantageously be used as starting material for the purification of a functional Factor H concentrate.

Other examples for applicable starting materials for caprylate precipitation are Cohn fraction I+III, equivalent fractions of the Kistler-Nitschmann process, e.g. precipitate B, the Cohn-Oncley process or the Hink process or solutions containing recombinantly produced Factor H, preferably expressed by a human cell-line like Human Embryonic Kidney cells (HEK), or transgenically expressed protein.

A major advantage of the present invention in comparison to prior art is the accomplishment of producing a preparation of complement Factor H of so far unknown activity and purity by a combination of few chromatographic steps. In comparison with commercially available preparations of complement Factor H (A137 from Complement Technology Inc. (CompTech); and Calbiochem) proteolytic cleavage products of the protein, typically accompanying plasmatic complement Factor H preparations, are kept minimal by this method displaying a maximal yield of native, fully glycosylated species of complement Factor H. The final complement Factor H concentrate deriving from this method yields a fully biologically functional protein in an in-vivo activity assay for complement Factor H.

The term 'functional complement Factor H' used herein refers to the capability of any tested complement Factor H-rich fraction to dose-dependently inhibit complement-mediated hemolysis of sheep erythrocytes incubated with complement Factor H-depleted serum.

Factor H containing caprylate precipitate is dissolved at about 4° C. in a buffer comprising 20-50 mM tri-sodium citrate, 20-120 mM glycine, 5-20 mM ethylene diamine tetra acetate (EDTA), 5-20 mM ethylene glycol tetraacetic acid (EGTA), pH 6.0-7.5, in particular in a buffer consisting of 20 mM tri-sodium citrate, 60 mM glycine, 10 mM EDTA, 10 mM EGTA at pH 7.4. Centrifugation at 4° C. for 20 minutes (5000-10000 rpm) separates non-dissolved material from supernatant.

The resultant supernatant is subsequently exposed to solvent/detergent (S/D) treatment. Therein, the supernatant is mixed with 0.3% (w/w) tri-n-butyl phosphate (TnBP) and 1% (w/w) Triton® X-100 (polyethylene glycol p-(1,1,3,3-tetramethylbutyl)-phenyl ether) for at least 40 minutes but up to 12 hours depending on temperature, in particular 50 minutes at room temperature to 4 hours at 4° C.

The solution is adjusted with 0.3N HCl to a pH of about 6.0 and diluted to a conductivity of 4.4 to 5.2 mS/cm at a temperature of 20-25° C. and filtered over 0.45 µm membranes. The filtered solution is subsequently applied to a gel/resin used for Cation Exchange Chromatography (CEX), such as, but not limited to, chromatographic materials with carboxymethyl or sulphonic-acid groups attached to a matrix material via a linking group, in particular to a strong cation exchange resin like Toyopearl® SP-650M of Tosho, i.e. a sulfoproyl group linked to a hydroxylated polyacrylic matrix. After sample application at room temperature weakly adsorbed proteins are removed from the gel by washing with several column volumes of equilibration buffer comprising 20 mM tri-sodium citrate at pH 6.0 and a conductivity of about 4.8 ms/cm at a temperature of 20-25° C. Said washing step is followed by step-gradient elution of bound protein fractions conducted by step-wise increase of sodium chloride (NaCl) concentration (0.1 M; 0.2 M; and 1M NaCl) in the same buffer. Fractions eluted from the CEX gel by equilibration buffer containing additionally 0.2M NaCl are pooled and the buffer is exchanged to a 20 mM Tris-HCL buffer (pH of 8.5-8.7 and conductivity of 0.1 to 0.5 mS/cm at 20-25° C. temperature).

The obtained solution is subjected to anion exchange chromatography (AEX). Resins useful for this type of chromatography are well known and consist of, but are not limited to, various amino groups, quaternary ammonium groups or methyl sulfonates linked to a matrix material, e.g. dextran, agarose, acrylic polymers or polystyrenes, in particular to a strong anion exchange resin such as Q-Sepharose® XL, having of quaternary ammonium groups linked to agarose.

After washing of Factor H adsorbed to the AEX resin with a buffer consisting of 20 mM TRIS at pH 8.6 step-gradient elution takes place by increasing the NaCl concentration in this buffer. Factor H is eluted from the anion exchange gel by an elution buffer comprising 20 mM TRIS-HCl and 0.25M NaCl at pH 6.8 while fractions eluted with a buffer containing 20 mM Tris-HCl and up to 0.2M NaCl were discarded.

The Factor H containing fraction was subjected to ultra/diafiltration for buffer exchange. Five times the sample volume was exchanged with a buffer comprising 5 mM sodium phosphate ($NaH_2PO_4 * 2 H_2O$) at pH 6.50 and a conductivity of 0.5 to 0.7 mS/cm at 20-25° C. This solution was subjected to ceramic hydroxyl-apatite chromatography (CHA). Ceramic hydroxyl-apatite presents hydroxyl- and phosphate-groups as well as calcium as functional groups on its surface, thus representing a mixed-mode chromatographic material, its ceramic features, i.e. high porosity compared to crystalline hydroxyl-apatite, are derived from its production process and provide much better separation due to higher specific surface area. A ceramic hydroxyl apatite with a dynamic binding capacity of >12.5 mg lysozyme/g and a nominal pore diameter of 800-1000 Angstroem, i.e. 80-100 nm, such as CHT® type II 40 µm from Bio-Rad®, was equilibrated with 10 mM sodium phosphate ($NaH_2PO_4 * 2 H_2O$) at pH 6.50 and a conductivity of about 1.1 mS/cm at 20-25° C. Linear gradient elution was performed with up to 1M NaCl in the equilibration buffer. Fractions eluting between a conductivity of 70-100 mS/cm at 20-25° C. were pooled for ultra/diafiltration.

As an option, an affinity chromatography, in particular with a resin wherein heparin is linked to the matrix, may be performed at this point in the purification process. If the heparin affinity chromatography is performed, the solution from the ceramic hydroxyl-apatite chromatography containing complement Factor H is subjected to ultra/diafiltration for buffer exchange with a buffer comprising 20 mM tri-sodium citrate at pH 6.0 with a conductivity of 4.5-4.7 mS/cm at 20-25° C. and is submitted onto a gel useable for heparin affinity chromatography, such as heparin coupled to agarose, one example of such a resin is Heparin Sepharose® 6 FF of GE Healthcare. After washing of gel and adsorbed complement Factor H with 5 column volumes of equilibration buffer, i.e. the same equilibration buffer as used for the buffer exchange directly prior, complement Factor H is eluted by addition of 0.2M NaCl in the same buffer.

Obtained Factor H solution, either from the ceramic hydroxyl-apatite chromatography or from the optional heparin-affinity chromatography is concentrated and formulated to the desired final concentration by ultra/diafiltration with a desired formulation buffer, e.g. phosphate buffered saline at a pH of about 7.4, to obtain a formulated Factor H concentrate of at least 10 mg/ml, e.g. about 50 mg/ml, in particular 10-300 mg/ml.

In order to improve pathogen safety it is also possible to introduce nanofiltration prior or post the concentration/formulation step by nanofilters of less than 35 nm porosity, such as nanofilters of 10-30 nm porosity, in particular of 20 nm or 15 nm porosity. The Factor H containing concentrate is sterile filtered and filled into final containers either after ultra/diafiltration for concentration and formulation purposes or after an optional nanofiltration, which takes place after the ultra/diafiltration for concentration and formulation purposes.

In order to provide besides a liquid product also a lyophilized product it is necessary to lyophilize Factor H concentrate already filled in final containers as final production step. The complement Factor H manufactured according to the process of this invention is obtained in good yield and up to now unknown purity and activity.

Assay for Testing Complement Factor H Activity

Principle of the Test

Testing the biological activity of complement Factor H is accomplished by an in vivo assay utilizing living sheep red blood cells as complement activator surfaces. These sheep erythrocytes are incubated with complement Factor H-depleted serum to supply the full range of serum complement components with simultaneous absence of this important regulator of the alternative pathway of complement. To assure only alternative complement activation to take place, these reagents are incubated with Veronal Buffered Saline (VBS) containing magnesium ions and EGTA.

Reconstitution of a source of complement Factor H protects sheep erythrocytes from complement-mediated hemolysis. The extent of hemolysis can be figured out by measuring the absorbance peak of exoplasmic hemoglobin at a wavelength of 414 nm. The specific activity of samples is calculated by comparison with a standard curve obtained by addition of a commercially available purified concentrate of complement Factor H. An example for this assay is provided in FIGS. 1 and 2 testing a complement Factor H eluate from the third purifying step of this method.

Description of the Complement Factor H Activity Test

First, 3 ml of sheep blood is washed with 10 ml of fresh Alsever's solution (4.2 g/L NaCl, 8 g/L tri-sodium citric acid*$2H_2O$, 0.55 g/L citric acid*$H_2O$ and 20.5 g/L D-Glucose) and is centrifuged at 2300 RPM at room temperature for 5 minutes. Absorbance of the supernatant is measured at 280 nm wavelength in spectrophotometer to monitor for protein release therein. Washing is continued three times until no increase in OD at 280 nm occurs.

The pellet comprising sheep erythrocytes is dissolved to give 33% solution in Alsever's solution.

Next, 10 µl of 33% sheep erythrocyte solution is mixed with 20 µl complement Factor H-depleted serum (A337, Complement Technology Inc.) in 500 µl vials at 4° C. and pre-incubated for 15 minutes at 4° C. After pre-incubation, different doses of standard complement Factor H (A137, Complement Technology Inc.) and of complement Factor H-rich samples are added as a volume of 20 µl. In order to equalize all sample and standard dilutions, remaining volume is filled by 0.9% NaCl solution.

Then, 30 µl of Veronal Buffered Saline (VBS) (2.5 mM sodium veronal, 144 mM NaCl, 10 mM ethylene glycol tetraacetic acid (EGTA), 30 mM $MgCl_2$, pH 7.4) is quickly added to all vials to start reaction (final reaction volume 80 µl). Vials are incubated for 30 minutes at 37° C. at 450 RPM. 220 µl of ice cold 2.5 mM sodium veronal, 144 mM NaCl and 10 mM EDTA, pH 7.4 is supplied to all vials to stop reaction to make a final volume of 300 µl per vial. All samples are centrifuged at 20000 g at room temperature for 5 minutes in Microfuge (Eppendorf) in order to separate cellular pellet from supernatant.

100 µl of supernatant is subjected in duplicate into wells of a 96 well microtitre plate (Nunc) and absorbance at 414 nm (extinction of exoplasmic hemoglobin in solution) is measured spectrophotometrically. Background lysis is subtracted from each sample as absorbance of VBS buffer and sheep erythrocytes only. A graphical illustration of absorbances and complement Factor H concentrations can be evaluated for complement Factor H activity.

Specificity of activity of a particular sample can be evaluated by incubation of the same sample dilutions with appropriate antibodies specific for complement Factor H known to block the protein's function (e.g. A100, Quidel, murine anti human complement Factor H monoclonal antibody).

EXAMPLES

Example 1

Factor H containing caprylate precipitate was dissolved at about 4° C. in a buffer comprising 20 mM tri-sodium citrate, 60 mM glycine, 10 mM ethylene diamine tetra acetate (EDTA), 10 mM ethylene glycol tetraacetic acid (EGTA), pH 7.4. Centrifugation at 4° C. for 20 minutes at about 5050 rpm, representing about 8000 g, separated non-dissolved material from supernatant.

The resultant supernatant was subsequently exposed to solvent/detergent (S/D) treatment. Therein, the supernatant is mixed with 0.3% (w/w) tri-n-butyl phosphate (TnBP) and 1% (w/w) Triton® X-100 (polyethylene glycol p-(1,1,3,3-tetramethylbutyl)-phenyl ether) for 60 minutes at room temperature.

The solution was adjusted with 0.3N HCl to a pH of 6.0 and diluted to a conductivity of 4.8 mS/cm at a temperature of 23° C. and filtered over 0.45 µm membranes. The filtered solution was subsequently applied to Toyopearl® SP-650M of Tosho. After sample application at room temperature weakly adsorbed proteins were removed from the gel by washing with several column volumes of equilibration buffer comprising 20 mM tri-sodium citrate at pH 6.0 and a conductivity of about 4.8 ms/cm at a temperature of 23° C. Said washing step was followed by step-gradient elution of bound protein fractions conducted by step-wise increase of sodium chloride (NaCl) concentration (0.1 M; 0.2 M; and 1M NaCl) in the same buffer. Fractions eluted from the gel by equilibration buffer containing additionally 0.2M NaCl were pooled and the buffer was exchanged to a 20 mM Tris-HCL buffer (pH of 8.6 and conductivity of 0.4 mS/cm at 24° C. temperature).

The obtained solution was subjected to anion exchange chromatography on Q-Sepharose® XL. After washing of Factor H adsorbed to the AEX resin with a buffer comprising 20 mM TRIS at pH 8.6 step-gradient elution took place by increasing the NaCl concentration in this buffer. Factor H was eluted from the anion exchange gel by an elution buffer comprising 20 mM TRIS-HCl and 0.25M NaCl at pH 6.8 while fractions eluted with a buffer containing 20 mM Tris-HCl and up to 0.2M NaCl were discarded.

The Factor H containing fraction was subjected to ultra/diafiltration for buffer exchange. Five times the sample volume was exchanged with a buffer comprising 5 mM sodium phosphate ($NaH_2PO_4*2\ H_2O$) at pH 6.50 with a conductivity of 0.6 mS/cm. This solution was subjected to ceramic hydroxyapatite chromatography (CHA).

A ceramic hydroxyl apatite, CHT® type II 40 µm from Bio-Rad®, was equilibrated with 10 mM sodium phosphate ($NaH_2PO_4*2\ H_2O$) at pH 6.5 and a conductivity of about 1.1 mS/cm at 22° C. Linear gradient elution was performed with up to 1M NaCl in the equilibration buffer. Fractions eluting between a conductivity of 70-100 mS/cm at 20-25° C. were pooled for ultra/diafiltration.

Obtained Factor H solution was concentrated to 20 mg/ml and formulated in phosphate buffered saline at a pH of 7.4.

Example 2

Essentially the same process as displayed in example 1 was performed but with slight deviations in temperatures of 1-2° C. and introduction of 20 nm nanofiltration at a Factor H concentration of 3 mg/ml as no blocking of filters was encountered it is obvious that nanofiltration at higher concentration is possible and desirable.

Example 3

Example 3 was essentially performed like example 1 but with a modified S/D treatment, namely 4 hours at 4° C., and heparin affinity chromatography introduced after ceramic hydroxyl-apatite chromatography. The complement Factor H containing fraction from ceramic hydroxyl-apatite chromatography was subjected to ultra/diafiltration for buffer exchange with a buffer comprising 20 mM tri-sodium citrate at pH 6.0 with a conductivity of 4.6 mS/cm at 23° C. and was afterwards submitted onto Heparin Sepharose® FF. After washing of gel and adsorbed complement Factor H with 5 column volumes of equilibration buffer, i.e. the same buffer as used for the buffer exchange, complement Factor H was eluted by addition of 0.2M NaCl to this buffer. Those fractions which eluted with the elution buffer were formulated and concentrated to 50 mg/ml.

Comparative Examples

Comparative Example 1

US 2008/0318841 A1; Paragraphs [0098] to [0109]; LFB

1. Anion exchange chromatography, 2. (non binding) heparin-affinity chromatography; 3. (binding) heparin-affinity chromatography, 4. first cation exchange chromatography, 5. second first cation exchange chromatography Information given was followed, unfortunately were just resins disclosed and some applied pH values, which were also followed in detail. As the application is silent about buffer compositions and concentrations, it was decided to use 20 mM tri-sodium citrate buffers adjusted with NaCl and HCl to given pH values and ion strengths estimated and controlled to fulfill given properties. Only deviation was the use of cryopoor plasma as starting material, which was introduced as cryoprecipitate supernatant.

Comparative Example 2

Preferred Embodiment of WO 2008/113 589 A1, Page 38; ZLB Behring

1. Heparin-affinity chromatography (heparin immobilized on HW-65-Toyopearl®), 2. PEG precipitation, 3. anion-exchange chromatography (Q-Sepharose® XL), 4. hydrophobic interaction chromatography (Butyl-Sepharose® FF)

Instructions were followed in detail with the resins disclosed.

Comparative Example 3

Mhatre et al. Process 1. first PEG precipitation, 2. second PEG precipitation, 3. anion exchange chromatography (DEAE-Sephacel®), 4. anion exchange chromatography (CM-Sepadex®), 5. size exclusion chromatography (Sephadex® G-200) Serum was prepared by recalcification of cryopoor plasma and centrifugation. Conditions were applied as disclosed with the slight modification of using DEAE-Sepharose® FF instead of DEAE-Sephacel®, CM-Sepharose® FF instead of CM-Sephadex® and Superdex®-200 instead of Sephadex® G-200). Resins used presented the same functional groups as those disclosed but possessed somewhat different carrier material.

Comparative Example 4

Lundwall et al. Process

1. Batch adsorption on anion exchange resin (QAE-Sephadex®), 2. second Batch adsorption on anion exchange resin (QAE-Sephadex®), 3. cation exchange chromatography (SP-Sephadex®), 4. anion exchange chromatography (DEAE-Sepharose®FF)

Process steps and conditions were closely followed throughout the purification with just one deviation, SP-650M-Toyopearl® was used for cation exchange chromatography instead of SP-Sephadex®.

Description of FIG. 1:

FIG. 1 depicts a 4-20% TRIS-glycine gradient SDS-Page (precast gels, Invitrogen™) with 5 µg protein applied per lane with silver staining according to the manufacturers manual (PlusOne Silver Staining Kit, Protein by GE Healthcare® and 4 minutes development).

Lane 1: Commercially available Factor H (CompTech, A137)

The most significant impurities are found at 75 kDa, approximately 105 kDa and at about 200 kDa.

Lane 2: Present invention, 4 chromatographic steps

The only band observed is the related to Factor H in the region of 150 kDa. No impurities are visible in the region of lower molecular weight, i.e. from Factor H to 10 kDa and beyond, as well as in the region of higher molecular weight, i.e. to 250 kDa and beyond up to the point of sample application.

Lane 3: Present invention, 3 chromatographic step steps

A dominating band is observed in the region of 150 kDa and relates to Factor H. No impurities are visible in the region of lower molecular weight, i.e. from Factor H to 10 kDa and beyond.

Lane 4: Factor H according to example of US 2008/0318841 A1

Several impurities are visible in the region of lower molecular weight, in particular from 100 kDa to 55 kDa with those at 55 kDa and 100 kDa being more pronounced. Additional impurities are found in the region of higher molecular weight, i.e. from about 200 kDa to the point of sample application.

Lane 5: Preferred embodiment of WO 2008/113 589 A1;

Several impurities are visible in the region of lower molecular weight, in particular from about 110 kDa to about 60 kDa with those around 100 kDa being somewhat stronger. Additional dominating impurities are found in the region of higher molecular weight, i.e. from about 180 kDa to the point of sample application, in particular at about 180 kDa, two bands at about 300 kDa and two bands half way between 250 kDa and the point of sample application.

Lane 6: Mhatre et al.

Two impurities are visible in the region of lower molecular weight, a slight but clearly visible one at about 55 kDa and a stronger one at 100 kDa. Additional impurities are found in the region of higher molecular weight presenting a region of clearly visible bands from about 180 kDa almost up to the point of sample application with the strongest band near the center of the region.

Lane 7: Lundwall et al.

Proteins are found everywhere from 50 kDa to up to the point of sample application with the strongest signal being the one of Factor H, but it can hardly be said to be dominating.

Lane 8: Commercially available Factor H (Calbiochem)

The most significant impurities are found at 75 kDa, approximately 105 kDa and at about 200 kDa. The impurities seem to be identical to those of the CompTech Factor H but a little bit stronger.

Western Blot of the same samples at comparable conditions, i.e. 4-20% TRIS-glycine gradient with 5 μg protein applied per lane, and polyclonal anti-human Factor H antibodies derived from goat (CompTech, A237) confirmed the identity of Factor H but revealed no significant differences between the various samples.

Figure 2A:
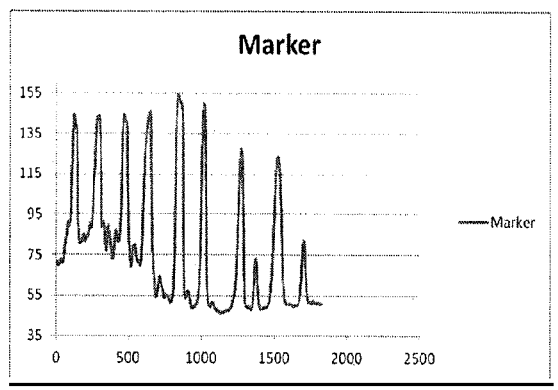

Description of FIG. 2A (the values at the axises represent arbitrary units):

FIG. 2A depicts the densitometric measurement of the marker lane of FIG. 1.

Figure 2B:
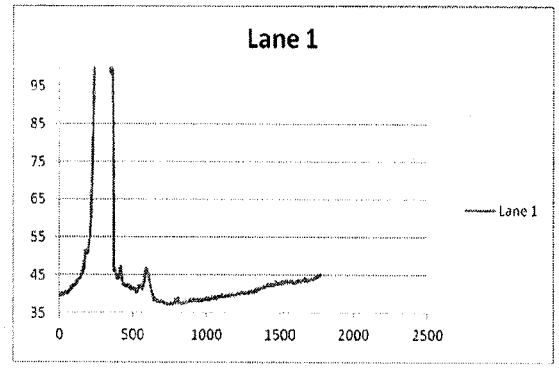

Description of FIG. 2B:

FIG. 2B depicts the densitometric measurement of lane 1 of FIG. 1 clearly showing impurities at data points about 400 and about 480 corresponding to impurities of 105 kDa and 75 kDa.

Figure 2C:
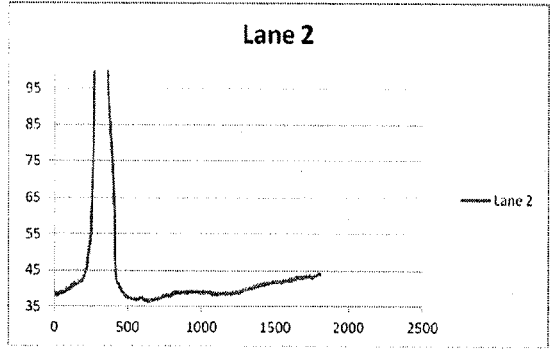
Figure 2D:
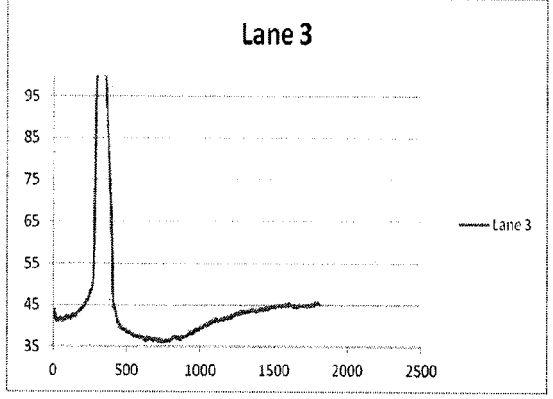

Description of FIGS. 2C and 2D:

FIG. 2C and FIG. 2D both depict the densitometric measurements of lane 2 and lane 3 of FIG. 1 of products of the invention with no proteinaceous impurities in the molecular weight range less than 110 kDa.

The invention claimed is:

1. A method for purification of complement Factor H from a complement Factor H containing source, which is a caprylate precipitate obtained by the addition of caprylate ions to fractions of blood or blood plasma, comprising the steps of:
   a. reconstituting the caprylate precipitate to provide a complement Factor H containing solution;
   b. performing a cation exchange chromatography;
   c. performing an anion exchange chromatography;
   d. performing a hydroxyl apatite chromatography;
   e. followed by ultra/diafiltration to obtain a complement Factor H concentrate.

2. The method according to claim 1 wherein a heparin affinity chromatography is performed.

3. The method according to claim 1 wherein the process comprises at least one of the following methods for pathogen removal and/or inactivation:
   a. solvent/detergent treatment;
   b. pasteurization,
   c. vapor heat treatment;
   d. dry heat treatment; or
   e. nanofiltration.

4. The method according to claim 1 wherein the complement Factor H concentrate is lyophilized.

5. The method of claim 1, wherein the cation exchange chromatography is the first chromatographic step.

* * * * *